United States Patent
Dahms

(10) Patent No.: US 6,171,600 B1
(45) Date of Patent: Jan. 9, 2001

(54) STABLE MULTIPLE X/O/Y-EMULSION

(75) Inventor: Gerd H. Dahms, Duisburg (DE)

(73) Assignee: IFAC GmbH, Velbert (DE)

( * ) Notice: Under 35 U.S.C. 154(b), the term of this patent shall be extended for 0 days.

(21) Appl. No.: 08/652,531

(22) PCT Filed: Nov. 29, 1994

(86) PCT No.: PCT/EP94/03955

§ 371 Date: May 23, 1997

§ 102(e) Date: May 23, 1997

(87) PCT Pub. No.: WO95/15143

PCT Pub. Date: Jun. 8, 1995

(30) Foreign Application Priority Data

Dec. 2, 1993 (DE) .................................................. 43 41 113

(51) Int. Cl.[7] .............................. A61K 9/113; B01J 13/00; C11D 3/386

(52) U.S. Cl. .......................... 424/401; 424/400; 510/417; 510/530; 514/943; 514/944; 516/54; 516/900; 516/928

(58) Field of Search .................................. 252/312, 314; 510/417, 530; 424/401; 514/943, 944

(56) References Cited

U.S. PATENT DOCUMENTS

| | | | |
|---|---|---|---|
| 3,702,302 | * 11/1972 | Wilson | 252/309 X |
| 4,254,105 | * 3/1981 | Fukuda | 514/943 X |
| 4,590,086 | * 5/1986 | Takahashi et al. | 252/312 X |
| 5,061,688 | * 10/1991 | Beissinger et al. | 252/312 X |
| 5,143,722 | * 9/1992 | Hollenberg et al. | 424/401 X |
| 5,304,334 | * 4/1994 | Lahanas et al. | 252/314 |
| 5,304,370 | 4/1994 | Hawkins | 424/70.2 |
| 5,478,561 | * 12/1995 | Ferrero | 424/401 |

FOREIGN PATENT DOCUMENTS

| | | |
|---|---|---|
| 4131678 A1 | 10/1992 | (DE) . |
| 345075 | 12/1989 | (EP) . |

OTHER PUBLICATIONS

M. Frenkel et al., "Multiple Emulsions," J. Colloid Interface Sci., vol. 94, pp. 174–178, 1982.

A.T. Florence et al., "The Formulation and Stability of Multiple Emulsions," Int. J. of Pharmaceutics, vol. 11, pp. 277–308, 1982.

S. Magdassi et al., "Correlation between Nature of Emulsifier and Multiple Emulsion Stability Drug Development and Industrial Pharmacy," vol. 11, pp. 791–798, 1985.

H. Linder, "Kollagen in der Kosmetik," Parfümerie and Kosmetic, vol. 65, pp. 340–343, 1984.

S. Magdassi, Correlation Between Nature and Emulsifier and Multiple Emulsion Stability, Drug Development and Industrial Pharmacy, vol. 11, 1985, pp. 791–798.

Patent Abstracts of Japan, vol. 8, No. 246, Nov. 10, 1984, & JP,A, 59 127.

M. Frenkle, Multiple Emulsions, Journal of Colloid and Interface Science, vol. 94, No. 1, Jul. 1983, pp. 174–178.

* cited by examiner

*Primary Examiner*—Richard D. Lovering
(74) *Attorney, Agent, or Firm*—McDermott, Will & Emery

(57) ABSTRACT

The stable multiple emulsion of the X/O/Y type contains at least one X/O phase in which X is an oil-immiscible component and O an oil phase. The X/O phase can contains an active substance, possibly in solid form, for example for medical, cosmetic or technical applications. The Y phase can be an aqueous phase, an aqueous liquid, preferably liquid-crystalline, gel or a W/O/W emulsion and serves as carrier for the at least one X/O phase. The X/O phase is produced using an emulsifier that has an HLB value equal to or less than 6 and/or is a W/O emulsifier. The preparation of the X/O phase itself and its diffusion in the Y phase are done with standard stirring tools. The drops of the X/O phase have long-term stability and, even when greatly diluted, do not interact with the Y phase or the drops or other X/O phases dispersed therein.

31 Claims, 1 Drawing Sheet

(1 of 1 Drawing Sheet(s) Filed in Color)

STABLE MULTIPLE X/O/Y-EMULSION

This application is a 371 of PCT/EP94/03955 filed Nov. 29, 1994.

The present invention relates to a stable multiple emulsion of the X/O/Y type.

Stable multiple emulsions of the W/O/W type are known, for example, from German Published Patent Application No. 4,131,678 and are described in a number of literature publications such as "Multiple Emulsions" by M. Frenkel et al. in J. Colloid Interface Sci., Vol. 94, pp. 174 to 178, 1982; "The Formulation and Stability of Multiple Emulsions" by A. T. Florence et al. in Int. J. of Pharmaceutics, Vol. 11, pp. 277 to 308, 1982; "Correlation between Nature of Emulsifier and Multiple Emulsion Stability" by S. Magdassi et al. in Drug Development and Industrial Pharmacy, Vol. 11, pp. 791 to 798, 1985.

Accordingly a multiple emulsion generally consists of a W/O phase, i.e. a water-in-oil phase comprising drops of a hydrophilic liquid which are dispersed in a hydrophobic liquid, and an aqueous phase in which these drops are dispersed. The internal component of the W/O phase may be constituted by, for example, an aqueous solution. The hydrophobic external component usually is selected from silicone oil, paraffin oil, triglyceride, fatty alcohol, ester oil or the like as well as mixtures thereof.

Such multiple emulsion can only be produced with the aid of emulsifiers. According to a generally acknowledged selection system, cf. Encyclopedia of Emulsion Technology, Ed. P. Becker, Marcel Dekker, New York, 1988, the emulsifiers are differentiated in accordance with an HLB value in correspondence with the ratio of their hydrophilic and hydrophobic portions; the HLB value is the hydrophilic portion percentage, divided by 5, of the emulsifier total molecular weight. Emulsifiers for forming W/O emulsions and having HLB values in the range of 3 to 6 are distinguished from emulsifiers forming wetting agents and having HLB values in the range of 7 to 9 and from emulsifiers for forming O/W emulsions and having HLB values in the range of 8 to 18.

In W/O/W emulsions of the initially mentioned type the aqueous phase is intended to serve as carrier for transporting the drops of the W/O phase to their place of action in a manner such that the compound present in the drops can not mix with or come into contact with the water. Important criteria therefore are the following:

1. Stability of the W/O phase against effects of temperature;
2. Stability of the W/O phase against coalescence;
3. Insensitivity to shearing forces occurring during preparation of the emulsion; and
4. Independence of the stability on the volume ratio of the W/O phase and the aqueous phase.

Hitherto known multiple emulsions satisfy these requirements only imperfectly; up to now, improvements could only be achieved by requiring passage through relatively complicated method steps when preparing the emulsion in order to be able to meet the desired stability requirements. Alternatively, specifically selected and composed emulsifiers had to be employed in order to realize the desired stability. According to the initially mentioned German Published Patent Application No. 4,131,678 a mixture of emulsifiers is required, one of which is a W/O emulsifier having an HLB value in the range of far below 3 to close to 5 and an other one of which has an HLB value in the range of 10 and far above.

Exclusively aqueous phases and oil phases were used in hitherto known W/O/W emulsions. The use of non-aqueous phases therein has never been considered.

In correspondence therewith it is the object of the invention to provide a simply composed multiple emulsion which can be produced in simple manner and which is significantly improved over known emulsions of the W/O/W type in terms of the afore noted stability criteria and its utility.

In particular, the inventive stable multiple emulsion should permit the inclusion of solids.

In order to achieve these objects, the invention provides a stable multiple emulsion of the X/O/Y type wherein X is a component immiscible with oil, O is an oil phase and Y is an aqueous phase, and which contains an emulsifier selected from the group of emulsifiers having an HLB value of $\geq 6$ and/or constituting a W/O emulsifier.

Advantageously, the emulsifier is selected from the group consisting of glycerol esters, sorbitan esters, sorbitol esters, polyglycerol esters, fatty alcohols, propylene glycol esters, alkyl glucoside esters, carbohydrate esters, lecithin, silicone copolymers, their mixtures or derivatives.

The emulsions prepared with the aid of one of such emulsifiers are obtained by means of a simple mixing operation with stirring whereby the stability of such multiple emulsions is affected neither by the inputted stirrer energy nor by the type of stirrer. In fact, any commercially available stirrer may be utilized for producing the inventive multiple emulsion.

The thus prepared multiple emulsions according to the invention possess long-time stability and meet the usual stability requirements in the temperature range of $-5°$ C. to $+45°$ C. The multiple emulsions according to the invention are stable in a highly water-diluted condition (1:100): Coalescence does not occur even after aggregation and creaming because the creamed material can be completely redispersed simply by shaking and the thus restored emulsion again is just as stable as the originally prepared emulsion.

The inventive stable multiple emulsions are particularly distinguished by the fact that the drops contained therein have a size distribution between 1 $\mu$m and 10 $\mu$m and thus have a relatively small, in fact, smaller drop size than the known multiple emulsions which is of considerable advantage for many applications.

In particular, however, according to the invention, it is possible dispersing a number of X/O phases separately from each other in the aqueous phase and therein long-time stability is given in the sense as noted hereinbefore. The drops of the different X/O phases will remain completely separated from each other and there does not occur any intermixing, exchange or the like with the external aqueous phase. This is of specific significance in all cases in which the X/O phases contain different active ingredients which are intended to be administered separately but in a common carrier in, for instance, medical or cosmetic applications.

For this purpose, the Y phase or aqueous phase preferably constitutes an aqueous liquid, an aqueous gel or a multiple W/O/W emulsion. In the latter case there is thus achieved the advantage that the W/O/W emulsion can be mixed with one or more X/O emulsions in almost any desired volume ratio without loss in stability which can not be achieved or only to a limited extent when using pure water.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

Figure 1:
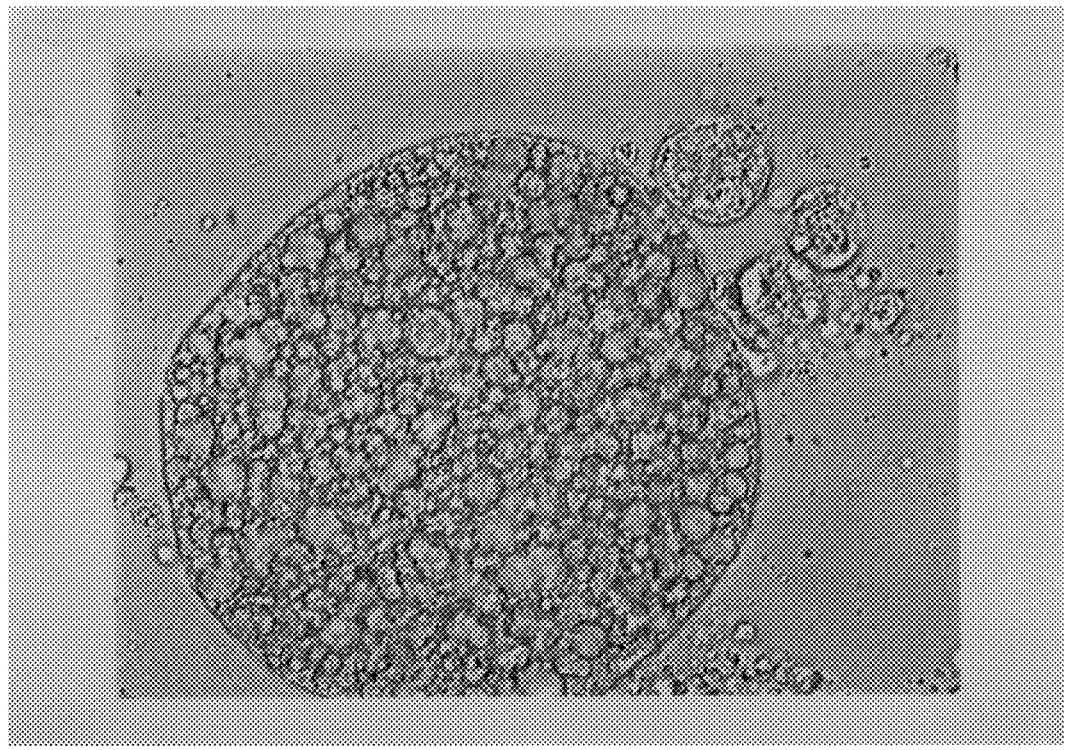
FIG. 1 (reproduction 1) shows the X/o/Y emulsion in phase contrast at 600-fold magnification.
Figure 2:
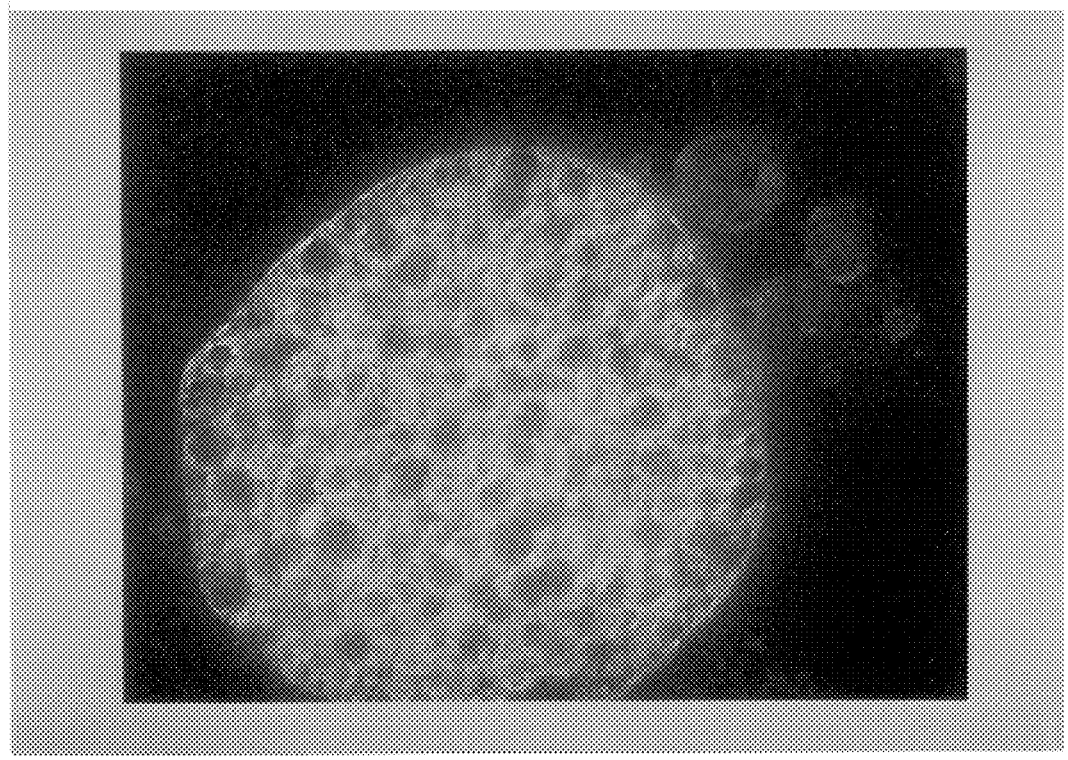
FIG. 2 (reproduction 2) shows the same microphotograph taken with polarized light.

Some inventive stable multiple emulsions will be described hereinbelow merely as a matter of example for more detailed explanation of the invention. All of the percentage data given therein for the various components are percent by weight of the total weight of the multiple emulsion=100. Given trivial names are taken from the CTFA index.

EXAMPLE 1

Using conventional vessels and stirrers, an oil phase and a water phase were prepared and heated to a mixing temperature in the range of 20° C. to 90° C., preferably 60° C. to 80° C. Thereafter, the heated oil phase and the heated water phase were combined with stirring by means of a conventional stirrer; after the combination, stirring is continued for a further minute. The thus obtained emulsion subsequently is cooled or left to cool to room temperature.

| The oil phase contained: | |
|---|---|
| sorbitan monostearate | 6.30% |
| laurylmethicon-copolyol | 2.70% |
| paraffin oil | 10.00% |
| The water phase contained | |
| demineralized water | 80.80% |
| phenonip | 0.20% |

In the following examples this emulsion will be designated as primary emulsion; the emulsion constitutes a multiple W/O/W emulsion and serves for preparing emulsions containing different X/O phases.

EXAMPLE 2

The multiple emulsion was prepared as described in Example 1; only the composition was different.

| The oil phase contained | |
|---|---|
| sorbitan monostearate | 4.50% |
| laurylmethicon-copolyol | 4.50% |
| paraffin oil | 10.00% |
| cyclomethicon | 10.00% |
| The water phase contained | |
| demineralized water | 70.80% |
| phenonip | 0.20% |

EXAMPLE 3

This Example was intended to demonstrate the immiscibility of different X/O phases by microscopic observation, the corresponding microphotographs being presented hereinbelow. This Example simultaneously also substantiates that finely divided solids like titanium dioxide can be dispersed in one of the emulsions and may serve as light protective filter in cosmetic preparations.

A secondary emulsion No. 1 was composed of an oil phase and a water phase.

| The oil phase contained | |
|---|---|
| laurylmethicon-copolyol | 1.5% |
| paraffin oil | 16.0% |
| TIOVEIL MOTG | 10.0%; |
| (titanium dioxide dispersed in mineral oil/triglyceride) | |

| The water phase contained | |
|---|---|
| water | 71.5% |
| sodium chloride | 1.0% | this secondary emulsion forms a W/O emulsion.

A secondary emulsion No. 2 contained an oil phase and an X component, namely

| cyclomethicon + dimethicon-copolyol | 15% |
|---|---|
| cyclomethicon (oil phase) | 30% |
| and | |
| propylene glycol (X component) | 55% | and thus forms an X/O emulsion.

The desired X/O/W emulsion, then, is obtained by heating the primary emulsion of Example 1 to a temperature in the range of 20° C. to 90° C., preferably 50° C. to 60° C.; thereafter, the secondary emulsions No. 1 and No. 2 are added one after the other with stirring and the mixture is cooled to room temperature.

The primary emulsion of Example 1 and the secondary emulsion No. 1 are combined in corresponding manner. After cooling to room temperature, samples are examined under a microscope; in the following reproductions of the microphotographs it will be clearly recognized that the drops of the primary emulsion and the secondary emulsion are present separately and side by side. This structure remains preserved even after long-time storage; even after aggregation and creaming followed by redispersion no change will be recognized.

The reproduction 1 shows the X/O/Y emulsion in phase contrast at 600-fold magnification. There will be recognized therein a large drop of the oil phase associated with the secondary emulsion No. 1 and surrounded by a water phase consisting of the water phase of the primary emulsion. The unstructured droplets of the water phase of the secondary emulsion No. 1 will be recognized within the large drop. These unstructured droplets are present within the oil phase associated with the secondary emulsion No. 1 and containing the titanium dioxide. Small oil drops are located outside of the large oil drop and formed by the oil phase of the primary W/O/W emulsion; small water drops are dispersed therein end will be recognized in the form of dark points. The two types of oil drops are clearly present separately and side by side and, as will be seen, the two oil phases do not mix with each other.

Reproduction 2 shows the same microphotograph taken with polarized light. Under these conditions the unstructured drops of the water phase associated with the primary emulsion appear dark whereas the titanium dioxide particles in the oil drop of the secondary emulsion No. 1 appear distinctly. The small oil drops located outside of the large oil drop appear only a little structured and are free of titanium dioxide particles; they will be recognized thereby as oil drops of the primary emulsion, water drops being only indistinctly visible within these oil drops.

The same results are obtained when the emulsifier laurylmethicon-copolyol in the secondary emulsion No. 1 and/or the emulsifier dimethicon-copolyol in the secondary emulsion No. 2 is replaced by any other emulsifier of the group of emulsifiers mentioned hereinabove on page 3.

EXAMPLE 4

This Example is intended to demonstrate that the multiple emulsions can be present not only in liquid form but also as a gel.

Therefore, a liquid-crystalline gel is first prepared from a gel-forming emulsifier phase and a water phase. The emulsifier phase and the water phase are separately heated to 80° C. Thereafter, the emulsifier phase is added with stirring to the water phase and the mixture is cooled to room temperature with continued stirring.

| The gel phase contained | |
|---|---|
| methylglucoside stearate | 10.0% |
| water | 89.8% |
| phenonip | 0.2% |

The thus obtained liquid-crystalline gel is heated to a temperature in the range of 20° C. to 90° C., preferably in the range of 50° C. to 60° C. and mixed with the secondary emulsions No.1 and No. 2 of Example 3 one after the other with stirring. The components were used in the following amounts, each in percent by weight of the total product=100:

| liquid-crystalline gel | 70% |
|---|---|
| secondary emulsion No. 1 | 20% |
| secondary emulsion No. 2 | 10% |

EXAMPLE 5

The liquid-crystalline phase obtained as in Example 4, is heated to a temperature in the range of 20° C. to 90° C., preferably 40° C. to 60° C.; thereafter, the secondary emulsions No. 1 and No. 2 of Example 3 and the primary emulsion of Example 1 are added one after the other to the heated liquid-crystalline gel with stirring, particularly in the amounts as given hereinbelow in percent by weight of the total product=100:

| liquid-crystalline phase | 80% |
|---|---|
| secondary emulsion No. 1 | 10% |
| secondary emulsion No. 2 | 5% |
| primary emulsion | 5% |

The aforementioned stable multiple emulsions are particularly suited as carriers for many types of active agents due to their stability and due to the stability of the drops contained therein, whereby the carrier may constitute an aqueous liquid as well as a liquid-crystalline gel or a primary emulsion of the W/O/W type in accordance with the Examples. In the following, it may be mentioned as a simple application example that it is desirable having present the washing agent for a washing machine in liquid form because liquid washing agents can be more readily metered than solid washing agents. Furthermore, it is desirable to add enzymes like proteases, lipases and amylases to the washing agent. Usually, however, such enzymes are not stable for long times in aqueous solution. The emulsion according to Example 3 offers a solution for the problem of providing a liquid enzyme-containing washing agent:

In this case the X/O phase is composed in correspondence with the secondary emulsion No.2 whereby the enzyme is dissolved in the polyol phase wherein the enzyme is stable for long times. When the thus formed X/O phase is dispersed in water conjointly with detergents, there is obtained a liquid washing agent wherein the enzyme is separated from the aqueous phase due to the fact that the interior of the drops, i.e. the polyol solution of the enzyme, is protected from contact and exchange with the aqueous phase by means of the emulsifier. The enzyme can be released only upon destruction of the emulsifier. In accordance with the selection of the emulsifier this can be achieved immediately at the start of the washing operation by breaking the emulsion either due to the prevailing temperature or due to the combined effects of the temperature and the shearing forces occurring during the washing operation.

The preparation of emulsions containing different X/O phases also permits placing mutually incompatible active agents into a common single carrier. In the field of cosmetics, for example, it is frequently desirable to apply to the skin mutually incompatible active agents like collagen preparations and urea. This is impossible under standard conditions, when using an aqueous carrier gel. Specifically, under such conditions, the collagen preparation would become denatured in the aqueous phase by the urea whereby it would be rendered ineffective, see "Kollagen in der Kosmetik" by H. Lindner in Parfumerie und Kosmetik, Vol. 65, pp.340–343; 1984. However, when the two active agents are separately applied to the skin, such denaturation will not ensue. This can be achieved by using an emulsion in correspondence with Example 4:

Both the active agents are dispersed in a common carrier gel under these conditions, the emulsifier again preventing the ingredients of the X/O phases from contacting or interacting with each other or with the carrier gel. In correspondence with Example 4, a carrier gel having a liquid-crystalline base is prepared; a secondary emulsion No. 1 is obtained in correspondence with Example 3 by dissolving urea instead of sodium chloride in the water phase and by dispensing with the titanium dioxide dispersion in the oil phase; in correspondence with the secondary emulsion No. 2 of Example 3, the collagen preparation is dissolved in the polyol phase which is, then, dispersed in the respective oil phase. The carrier gel, which is prepared according to Example 4, then, contains the two active agents in the oil drops associated with the different X/O phases and separated from each other in the absence of mutual exchange or exchange with the aqueous carrier gel so that the total product is stable for long times. When applied to the skin the emulsion will be broken, however, the two active agents are resorbed by the skin in different manner and at a rate such that denaturation of the collagen preparation does not occur despite the common application.

In corresponding manner also drugs which are effective at different locations, can be dispersed in different X/O phases which, in turn, can be dispersed in a common carrier as described in Example 3. It is thus possible to place into a common liquid carrier, for example, pharmaceutical agents which are intended to become effective at different locations of the digestive tract. This is achieved by using different emulsifiers for preparing the respective X/O phases which emulsifiers are unstable under conditions prevailing at the respective locations of action. The active agents present in the drops of the X/O phases, are then released thereby.

For instance, there can be prepared a first X/O phase wherein the oil-immiscible component constitutes an aqueous solution of an active agent and the used emulsifier is an emulsifier which rapidly hydrolyzes in an acid medium. Furthermore, a second X/O phase corresponding to the secondary emulsion No. 2 according to Example 3 is obtained whereby the employed emulsifier is an acid-stable emulsifier such as a silicone copolymer. Both the X/O phases are dispersed in water which forms the carrier liquid.

After oral administration, the emulsifier present in the first X/O phase is hydrolyzed under the action of gastric acid so that the active agent present in this X/O phase will be released in the stomach. The emulsifier present in the second X/O phase is stable under these conditions so that the second X/O phase passes unchanged through the stomach. Much more, the respective active agent will only be released thereafter in the digestive tract, namely in a section where the emulsifier is degraded or dissolved. The selection of emulsifiers can be readily adapted to the conditions prevailing at the locations of action.

The oil phase and/or the X component may contain solids such as pigments, microspheres, silica gel or wax. Pigments may serve as light protective filters (for instance, in the field of cosmetics), microspheres or silica gel may be utilized as carriers for active agents, and wax can be used as a base of, for example, a polish.

It will be self-evident that, during preparation of emulsions containing active agents of the aforementioned type, it will be readily possible to add to the emulsions, apart from the active agents as such, all other adjuvants and additives as required for the respective purpose of use.

What is claimed is:

1. Stable multiple emulsion of the X/O/Y type in which X constitutes a component immiscible with oil and O is an oil phase and Y an aqueous phase and which contains at least one emulsifier selected from the group consisting of emulsifiers having an HLB value $\leq 6$ and/or a W/O emulsifier with the proviso that no water-soluble emulsifier is present in the aqueous phase when a W/O emulsion is dispersed therein.

2. Stable multiple emulsion according to claim 1, characterized in that the aqueous phase constitutes an aqueous liquid, an aqueous gel or a multiple W/O/W emulsion.

3. Stable multiple emulsion according to claim 2, characterized in that the gel is formed using an emulsifier forming a liquid-crystalline network.

4. Stable multiple emulsion according to claim 1, characterized in that the emulsifier is selected from the group consisting of glycerol esters, sorbitan esters, sorbitol esters, polyglycerol esters, fatty alcohols, propylene glycol esters, alkyl glucoside esters, carbohydrate esters, lecithin, silicone copolymers and their mixtures.

5. Stable multiple emulsion according to claim 4, characterized in that the esters are formed of long-chain saturated fatty acids or a mixture of long-chain saturated and unsaturated fatty acids which mixture is solid at room temperature.

6. Stable multiple emulsion according to claim 1, characterized in that the oil phase is selected from the group consisting of silicone oils, paraffin oils, triglycerides, fatty alcohols, ester oils and mixtures thereof.

7. Stable multiple emulsion according to claim 6, characterized in that the oil phase contains a solid selected from the group consisting of pigments, microspheres, silica gel, and wax.

8. Stable multiple emulsion according to claim 1, characterized in that the X component constitutes a polyol miscible with water.

9. Stable multiple emulsion according to claim 8, characterized in that the polyol is selected from the group consisting of propylene glycol, butylene glycol, polyalkylene glycol, glycerol, polyglycerol and mixtures thereof.

10. Stable multiple emulsion according to claim 8, characterized in that the X component contains an active agent selected from the group consisting of pharmaceutical agents, cosmetic agents, and agents relating to washing, food or agricultural technology.

11. Stable multiple emulsion according to claim 8, characterized in that the X component contains a solid selected from the group consisting of pigments, microspheres, silica gel, and wax.

12. Stable multiple emulsion according to claim 1, characterized in that a number of X components are provided and dispersed in respective oil phases, the thus formed different X/O phases being present in the X/O/Y emulsion side by side and permanently separated from each other.

13. Stable multiple emulsion according to any one of the preceding claims, characterized in that the X/O phase is formed of drops having a diameter in the range of 1 $\mu$m to 10 $\mu$m.

14. Method of preparing a stable multiple emulsion of the X/O/Y type in which X is a component immiscible with oil, O is an oil phase and Y an aqueous phase and which contains at least one emulsifier, wherein the emulsifier is selected from the group consisting of emulsifiers having an HLB value $\leq 6$ and/or a W/O emulsifier, with the proviso that no water-soluble emulsifier is present in the aqueous phase when a W/O emulsion is dispersed therein comprising the steps of mixing an X/O phase and the aqueous phase, said phases being preheated to 20° C. to 90° C. before mixing; and cooling the mixture to room temperature.

15. Method according to claim 14, characterized in that the X/O phase and the aqueous phase are separately heated to a temperature in the range of 60° C. to 80° C.

16. Method according to claim 14, characterized in that the aqueous phase is selected from the group consisting of an aqueous liquid, an aqueous gel and a multiple W/O/W emulsion.

17. Method according to claim 16, characterized in that the gel is formed by using an emulsifier which forms a liquid-crystalline network.

18. Method according to claim 14; characterized in that a first X/O/Y emulsion is heated to a temperature in the range of 20° C. to 90° C. and mixed with stirring with a second X/O/Y emulsion which has been prepared in the same manner, and that the mixture is cooled to room temperature.

19. Method according to claim 18, characterized in that the first X/O/Y emulsion is heated to a temperature in the range of 50° C. to 60° C.

20. Method for preparing a stable multiple emulsion of claim 14 in which the X/O phase contains a pharmaceutical agent, a cosmetic agent or an active agent relating to the washing, food or agricultural technology.

21. Method for preparing a stable multiple emulsion of claim 14 wherein the stable multiple emulsion contains a number of X/O phases which are present side by side separately from each other.

22. Method of claim 21, characterized in that the number of X/O phases, which are present side by side separately from each other, contain respective active agents which differ from each other.

23. Method according to claim 14, characterized in that the emulsifier is selected from the group consisting of glycerol esters, sorbitan esters, sorbitol esters, polyglycerol esters, fatty alcohols, propylene glycol esters, alkyl glucoside esters, carbohydrate esters, lecithin, silicone copolymers and their mixtures.

24. Method according to claim 23, characterized in that the esters are formed of long-chain saturated fatty acids or a mixture of long-chain saturated and unsaturated fatty acids which mixture is solid at room temperature.

25. Method according to claim 14, characterized in that the oil phase is selected from the group consisting of silicone oils, paraffin oils, triglycerides, fatty alcohols, ester oils and mixture thereof.

26. Method according to claim 25, characterized in that the oil phase contains a solid selected from the group consisting of pigments, microspheres, silica gel, and wax.

27. Method according to claim 14, characterized in that the X component constitutes a polyol miscible with water.

28. Method according to claim 27, characterized in that the polyol is selected from the group consisting of propylene glycol, butylene glycol, polyalkylene glycol, glycerol, polyglycerol and mixtures thereof.

29. Method according to claim 27, characterized in that an active agent is added to the X component and selected from the group consisting of pharmaceutical agents, cosmetic agents and active agents relating to washing, food or agricultural technology.

30. Method according to claim 27, characterized in that the X component contains a solid selected from the group consisting of pigments, microspheres, silica gel, and wax.

31. Method according to claim 14, characterized in that the X/O phase is dispersed to form drops having a diameter in the range of 1 $\mu$m to 10 $\mu$m.

* * * * *